United States Patent [19]

Angerbauer et al.

[11] Patent Number: 4,880,795
[45] Date of Patent: Nov. 14, 1989

[54] CEPHALOSPORINS

[75] Inventors: Rolf Angerbauer; Michael Boberg; Karl G. Metzger, all of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 21,293

[22] Filed: Mar. 3, 1987

Related U.S. Application Data

[62] Division of Ser. No. 730,985, May 6, 1985, Pat. No. 4,686,216.

[51] Int. Cl.$^4$ .................. A61K 31/545; C07D 501/46
[52] U.S. Cl. ..................................... 514/202; 540/222
[58] Field of Search ........................ 514/202; 540/222

[56] References Cited

U.S. PATENT DOCUMENTS 4,525,473 6/1985 Aburaki ............................... 514/202
4,686,216 8/1987 Angerbauer ........................ 514/202

FOREIGN PATENT DOCUMENTS 3419013 11/1985 Fed. Rep. of Germany .

OTHER PUBLICATIONS

Angerbauer, R., Chem. Abstract, 105:42519c, (Abstract of FRG 3,419,014).

*Primary Examiner*—Donald G. Daus
*Attorney, Agent, or Firm*—Sprung Horn Kramer & Woods

[57] ABSTRACT

Novel cephalosporins of the formula

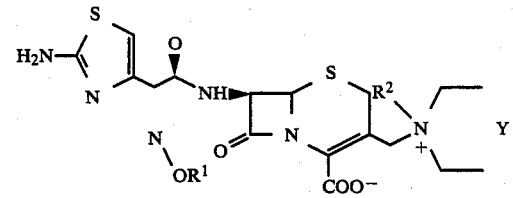

in which
R$^1$ is an aliphatic or cycloaliphatic hydrocarbyl radical of up to 6 carbon atoms which is optionally substituted by a carboxyl group,

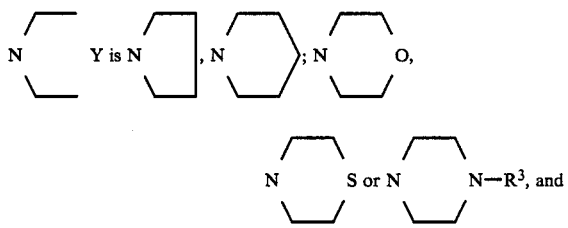

R$^2$ and R$^3$ each independently is an optionally substituted aliphatic or cycloaliphatic hydrocarbyl radical of up to 6 carbon atoms, but is not unsubstituted methyl, or pharmaceutically acceptable salts thereof, are effective antibacterially and promote the growth of animals.

5 Claims, No Drawings

CEPHALOSPORINS

This is a division of application Ser. No. 730,985, filed May 6, 1985, now U.S. Pat. No. 4,686,216.

The invention relates to new cephalosporins, their use as medicaments, in particular in antibacterial therapy, and processes for their preparation.

Cephalosporins which contain a 2-(2-aminothiazol-4-yl)-2-alkoxyiminoacetic acid radical as an acyl side chain and a pyridiniummethyl radical in the 3-position are known from European Patent No. 64,740.

The present invention provides cephalosporins of the general formula I and their pharmaceutically acceptable salts

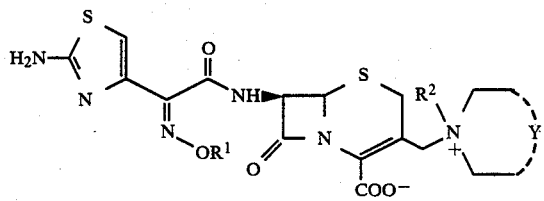
(I)

in which $R^1$ represents a $C_1$-$C_6$-alkyl radical, which can be straight-chain, branched or cyclic and also unsaturated and can be substituted by a carboxyl group, $R^2$ represents a $C_1$-$C_6$-alkyl radical, which can be straight-chain, branched or cyclic, unsaturated and optionally substituted, but which cannot represent an unsubstituted methyl radical, and

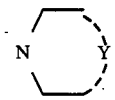

represents a radical of the formula

wherein $R^3$ has the meaning given above for $R^2$.

Preferred compounds of the formula I are those in which $R^1$ and

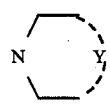

have the meaning given and $R^2$ represents a $C_1$-$C_6$-alkyl radical, which can be straight-chain, branched or cyclic and unsaturated and which can be monosubstituted or polysubstituted, preferably monosubstituted, by hydroxyl, carboxyl, $C_1$-$C_4$-alkoxycarbonyl, $C_1$-$C_4$-alkylcarbonyl, carbamoyl, sulpho, cyano, nitro, amino, halogen, $C_1$-$C_4$-alkyl- and -dialkylamino, $C_1$-$C_4$-alkylcarbonylamino, $C_1$-$C_4$-alkoxy, $C_1$-$C_4$-alkylthio, $C_1$-$C_4$-alkylsulphinyl and $C_1$-$C_4$-alkylsulphonyl, with the proviso that $R^2$ cannot be an unsubstituted methyl radical.

Particularly preferred compounds are those in which $R^1$ and

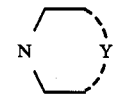

have the meaning given and $R^2$ represents a $C_1$-$C_4$-alkyl radical, which can be straight-chain, branched or cyclic and unsaturated and which can be substituted by hydroxyl, carboxyl, $C_1$-$C_4$-alkoxy, halogen, nitro and amino, with the proviso that $R^2$ cannot be an unsubstituted methyl radical.

Very particularly preferred compounds of the formula I are those
in which $R^1$ represents a $C_1$-$C_3$-alkyl radical, preferably methyl, $R^2$ represents an optionally substituted $C_1$-$C_4$-alkyl radical, such as, in particular, ethyl, propyl, isopropyl, cyclopropyl, hydroxyethyl, chloroethyl, methoxymethyl, methoxyethyl, vinyl, allyl, carboxyethyl or aminoethyl, but not unsubstituted methyl, and

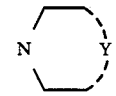

has the abovementioned meaning.

The compounds of the general formula I can be obtained by a process in which compounds of the general formula II

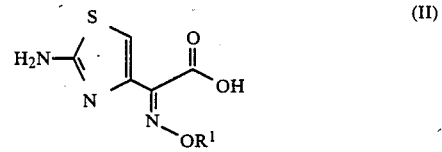
(II)

wherein $R^1$ has the abovementioned meaning, in which the amine group can be protected or unprotected, are reacted, after activation of the carboxyl group by conversion into a mixed anhydride, for example with ethyl chloroformate or methanesulphonyl chloride, after conversion into the acid halide or after conversion into an activated ester with, for example, N-hydroxybenzotriazole and dicyclohexylcarbodiimide, with compounds of the general formula III

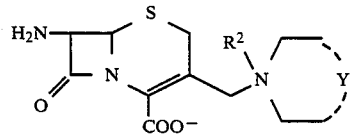
(III)

wherein $R^2$ and

have the abovementioned meaning, and, if appropriate, the protective groups are then split off and the desired salts or, from salts, the free acids are prepared.

A large number of methods known from cephalosporin or penicillin chemistry can be used for the coupling of carboxylic acids (II) to β-lactams of the formula (III). It has proved advantageous to activate the carboxylic acids of the general formula (II) without the amine-protective group and then to couple the activated product with β-lactams of the formula (III), which have been dissolved as salts with an amine. Activation with sulphonic acid derivatives of the formula (V) to anhydrides of the formula (IV) is particularly advantageous:

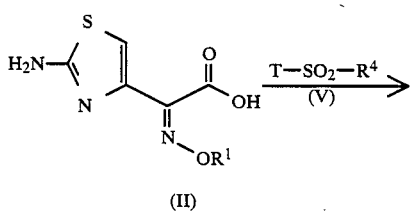

wherein

T represents a radical $R^4$-$SO_2$-O- or halogen and $R^4$ denotes an alkyl radical which has 1-10 C atoms and can optionally be substituted by fluorine, chlorine, CN, phenyl, alkoxycarbonyl, alkoxy or alkyl, it being possible for the latter alkyl radicals to carry 1-4 C atoms, or a phenyl radical, which can optionally be substituted by fluorine, chlorine, bromine, CN, alkyl, alkoxy, alkylthio, alkoxycarbonyl—it being possible for the latter alkyl groups to carry 1-4 C atoms—nitro, trifluoromethyl and phenyl.

If $R^4$ is substituted, 1-3 substituents, preferably those mentioned, are preferably present.

$R^4$ very particularly preferably represents a methyl or p-tolyl radical.

The mixed anhydrides of the formula (IV) are prepared by dissolving the carboxylic acids of the formula (II) with 1-1.4 equivalents of an amine in a solvent and reacting them with 1 to 1.2 equivalents of a sulphonic acid derivative of the formula (V).

Suitable solvents are all the solvents which are stable under the reaction conditions, such as, for example, diethyl ether, tetrahydrofuran, acetonitrile, acetone, methylene chloride, chloroform or dimethylformamide.

Suitable amines are tertiary amines, such as, for example, triethylamine or tributylamine, and also sterically hindered secondary amines, such as, for example, diisopropylamine.

The reactions can be carried out at temperatures between −80° C. and room temperature, low temperatures avoiding isomerization of the substituents on the double bond. The activation is advantageously carried out with Cl-$SO_2CH_3$ in dimethylformamide at −40° to −60° C. in the course of 0.2 to 24 hours, preferably 0.5 to 5 hours.

The solvents mentioned for the preparation of the compounds of the formula (IV) or water can be used to dissolve the compounds of the formula (III), and the amines mentioned in the above preparation can be used as the base.

Activation of the carboxylic acids of the general formula (II) by conversion into an activated ester with, for example, N-hydroxysuccinimide and dicyclohexylcarbodiimide or 1-hydroxybenzotriazole and dicyclohexylcarbodiimide is also particularly advantageous.

Suitable solvents are all the solvents which are also suitable for the preparation of anhydrides of the formula (IV).

The reactions can be carried out at temperatures between −30° C. and +100° C. Advantageously, activation is carried out with 1-hydroxybenzotriazole and dicyclohexylcarbodiimide in dimethylformamide at room temperature for 2 to 6 hours, the dicyclohexylurea which has precipitated is then filtered off with suction and the reaction with a compound of the formula (III) in the form of a solution of its amine salt is carried out in the course of 2 to 24 hours. The solvents mentioned for the preparation of the compounds of the formula (IV) can be used to dissolve the compounds of the formula (III), and the amines mentioned in the above preparation can be used as the base.

The compounds of the formula (III) are obtained by splitting off the amine-protective group $R^5$ from compounds of the formula (VI).

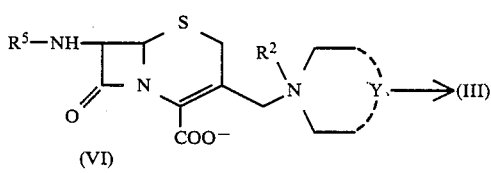

$R^5$ here can be either a protective group which is unstable towards acids, such as the t-butoxycarbonyl group, or, advantageously, a protective group which can be split off enzymatically. Preferred protective groups which can be split off enzymatically are phenacetyl or 2-thienylacetyl.

The enzymatic splitting off is carried out at room temperature in water or a mixture of water and a polar organic solvent, such as, for example, acetonitrile or tetrahydrofuran, with immobilized penicillin G acylase at pH 7-8, preferably at pH 7.5-7.8.

During the enzymatic splitting, the pH value is kept constant by addition of a base, such as lithium hydroxide, sodium hydroxide, potassium hydroxide or a tertiary amine, such as, for example, triethylamine, tripropylamine, tributylamine or pyridine.

The compounds of the formula (VI) can be prepared from esters of the formula (VII) via intermediate compounds of the formula (VIII).

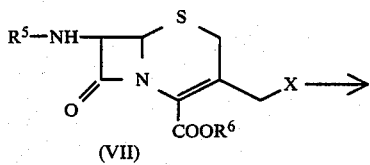
(VII)

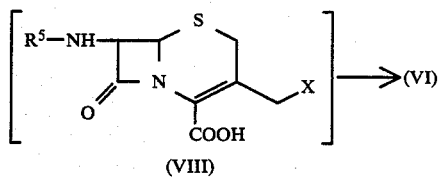
(VIII)

In the esters of the formula (VII), X represents a leaving group, such as mesylate, tosylate, brosylate, triflate, nonaflate, iodide, bromide or chloride, and $R^6$ represents an acid-protective group which is customary in cephalosporin chemistry, preferably a protective group which can be split off under acid conditions, such as, for example, benzhydryl, 4-methoxydiphenylmethyl or t-butyl.

The compounds of the formula (VII) are converted into the reactive free acids of the formula (VIII) by splitting off the acid-protective group $R^6$. In the case of the preferred protective groups $R^6$ which are unstable towards acids, the protective group is split off in an organic solvent. Preferably, the benzhydryl protective group is split off in methylene chloride with trifluoroacetic acid, possibly with the addition of an alkoxybenzene, preferably methoxybenzene. The elimination reaction is carried out at −20° C. to +30° C., preferably 0° C., in the course of 5 minutes to one hour, preferably in the course of 20 minutes.

The acid of the formula (VIII) can be isolated after the protective group has been split off. Advantageously, however, the product is not isolated but is converted directly, without purification, into compounds of the formula (VI). For this, the solution of (VIII) formed in the reaction (VII)→(VIII) is concentrated under mild conditions in vacuo. The crude acid which remains is taken up in an organic solvent, preferably in tetrahydrofuran, and reacted with 2–50 equivalents, preferably with 5–20 equivalents, of a tertiary amine of the formula

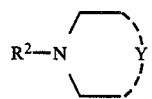

wherein
$R^2$ and

have the abovementioned meaning, to give compounds of the formula (VI).

The reaction is carried out at temperatures between −20° C. and 40° C., preferably at 25° C., in the course of 10 minutes to two hours, preferably in the course of 30 minutes. When the reaction has ended, the product can be precipitated by addition of diethyl ether. The crude product thus obtained can be purified on a resin, such as Diaion HP 20 or XAD 7. It is also advantageously possible to further convert the crude product directly into compounds of the formula (III).

Alternatively, the compounds of the formula (VI) can be prepared from acids of the formula (IX) in which $R^5$ has the abovementioned meaning and $R^7$ represents

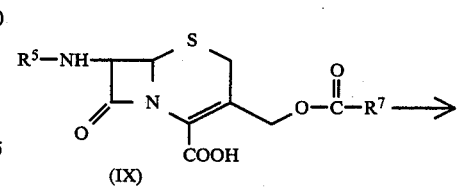
(IX)

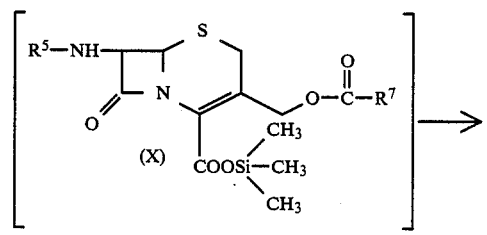
(X)

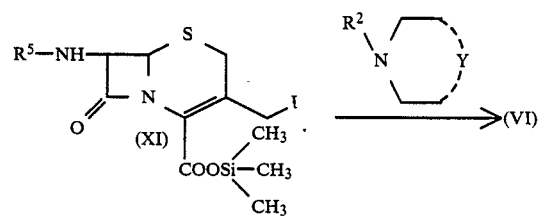
(XI)

an optionally substituted alkyl or aryl radical, such as methyl, ethyl, propyl, chloromethyl, dichloromethyl, trichloromethyl, trifluoromethyl or phenyl. $R^7$ very particularly preferably represents a methyl group.

The starting compounds of the formula (IX) are suspended in a suitable organic solvent and are dissolved by silylation to the silyl ester XI. Particularly suitable organic solvents are chloroform, methylene chloride and dichlorethane. The silylation is carried out with a customary silylating agent, such as trimethylchlorosilane (TMCS), hexamethyldisilazane (HMDS), N,O-bis-(trimethylsilyl)acetamide (BSA), N,O-bis-(trimethylsilyl)-trifluoroacetamide (BSTFA), N-methyl-N-trimethylsilylacetamide (MSA), N-methyl-N-trimethylsilyltrifluoroacetamide (MSTFA), 1,3-bis-(trimethylsilyl)urea or trimethylsilyltrifluoromethanesulphonate. A mixture of several silylating agents can also be employed here.

The silylation is carried out at −30° C. to +70° C., preferably at −10° C. to +10° C., in the course of 5 minutes to 30 minutes. An excess of up to ten-fold of the silylating agent, preferably a two-fold to five-fold excess, is advantageously employed.

The solution thus obtained of the trimethylsilyl ester of the formula (X) is reacted with one to ten equivalents, preferably with three to four equivalents, of a trialkylsilyl iodide, particularly preferably trimethylsilyl iodide, at −40° C. to +30° C., preferably at −10° C. to +10° C., in the course of 15 minutes to 2 hours, preferably in the course of 30 minutes to 1 hour, to give compounds of the formula (XI).

The compounds of the formula XI are advantageously not isolated, but reacted directly, without purification, with amines

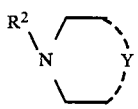

to give the compounds of the formula VI.

Alternatively, the compounds of the general formula I can also be prepared by reacting compounds of the formula (XII)

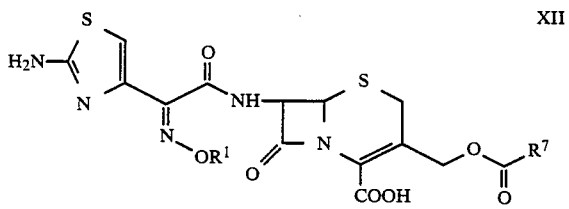

in which $R^1$ and $R^7$ have the abovementioned meaning, directly, without isolating the intermediate stages, after silylation and conversion into the iodide, with amines

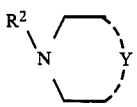

to give compounds of the formula I, in a manner analogous to that described above for the conversion of compounds of the formula X into compounds of the formula VI.

The compounds according to the invention exhibit a powerful and broad antimicrobial activity, in particular against Gram-negative and Gram-positive bacteria. These properties enable them to be used as chemotherapeutic active compounds in medicine.

The compounds according to the invention are particularly effective against bacteria and bacteria-like microorganisms. They are therefore particularly suitable in human and veterinary medicine for the prophylaxis and chemotherapy of local and systemic infections caused by these pathogens.

For example, local and/or systemic diseases which are caused by the following pathogens or by mixtures of the following pathogens can be treated and/or prevented: Micrococcaceae, such as Staphylococci, for example *Staphylococcus aureus, Staph. epidermidis* and *Staph. aerogenes,* and *Graffkya tetragena* (Staph.=Staphylococcus); Lactobacteriaceae, such as Streptococci, for example *Streptococcus pyogenes,* α- and β-haemolyzing Streptococci, non-(γ-)-haemolyzing Streptococci, *Str. viridans* and *Str. faecalis* (Enterococci) and *Dipolococcus pneumoniae* (Pneumococci)(Str.=Streptococcus); Enterobacteriaceae, such as Escherichiae bacteria of the Coli group: Escherichia bacteria, for example *Escherichia coli,* Enterobacter bacteria, for example *E. aerogenes and E. cloacae,* Klebsiella bacteria, for example *K. pneumoniae,* Serratia, for example *Serrathia marcescens* (E.=Enterobacter) (K.=Klebsiella), Proteae bacteria of the Proteus group: for example *Proteus vulgaris, Pr. morganii, Pr. rettgeri* and *Pr. mirabilis* (Pr.=Proteus); Pseudomonadaceae, such as Pseudomonas bacteria, for example *Pseudomonas aeruginosa* (Ps.=Pseudomonas); and Bacteroidaceae, such as Bacteroides bacteria, for example *Bacteroides fragilis* (B.=Bacteroides).

The above list of pathogens is purely illustrative and is in no way to be interpreted as restrictive.

Examples which may be mentioned of diseases which can be prevented, alleviated and/or cured by the compounds according to the invention are: diseases of the respiratory tract and pharyngeal cavity; otitis and pharyngitis; pneumonia; peritonitis and pyelonephritis; cystitis and endocarditis; systemic infections; bronchitis; arthritis; and local infections.

The present invention includes pharmaceutical formulations which, in addition to non-toxic, inert, pharmaceutically suitable excipients, contain one or more compounds according to the invention or which consist of one or more active compounds according to the invention, as well as processes for the preparation of these formulations.

The present invention also includes pharmaceutical formulations in dosage units. This means that the formulation is in the form of individual parts, for example tablets, dragees, capsules, pills, suppositories and ampules, the active compound contents of which correspond to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, one third or one quarter of a daily dose.

By non-toxic, inert, pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium and magnesium stearate and solid polyethylene glycols, or mixtures of the substances listed under (a) to (i).

The tablets, dragees, capsules, pills and granules can be provided with the usual coatings and shells, optionally containing opacifying agents, and can also be of such composition that they release the active compound or compounds only, or preferentially, in a certain part of the intestinal tract, if appropriate in a delayed manner, examples of embedding compositions which can be used being polymeric substances and waxes.

The active compound or compounds, optionally together with one or more of the abovementioned excipients, can also be in microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

For parenteral administration, the solutions can also be in a sterile form which is isotonic with blood.

The therapeutically active compounds should preferably be present in the abovementioned pharmaceutical formulations in a concentration of about 0.1 to 99.5% by weight, preferably about 0.5 to 95% by weight of the total mixture.

The abovementioned pharmaceutical formulations can also contain other pharmaceutical active compounds, in addition to the compounds according to the invention.

The abovementioned pharmaceutical formulations are prepared in the customary manner by known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds according to the invention in total amounts of about 1 to about 1,000, preferably 1 to 200 mg/kg of body weight every 24 hours, if appropriate in the form of several individual administrations, in order to achieve the desired results. An individual administration preferably contains the active compound or compounds according to the invention in amounts of about 1 to about 250, in particular 1 to 60 mg/kg of body weight. However, it may be necessary to deviate from the dosages mentioned, and in particular to do so as a function of the species and body weight of the subject to be treated, the nature and severity of the diseases, the nature of the formulation and of the administration of the medicament and the period or interval over which administration takes place. Thus, it can in some cases be sufficient to manage with less than the abovementioned amount of active compound, while in other cases the abovementioned amount of active compound must be exceeded. The particular optimum dosage required and the mode of administration of the active compounds can easily be determined by anyone skilled in the art on the basis of his expert knowledge.

In order to extend the action spectrum, the active compounds according to the invention can be combined with another β-lactam antibiotic or also with aminoglycoside antibiotics, such as, for example, gentamicin, sisomicin, kanamycin, amikacin or tobramycin.

The active compounds according to the invention can be used in all fields of animal breeding as agents for promoting and accelerating growth and for improving the feed utilisation of healthy and sick animals.

The activity of the active compounds here is largely independent of the species and sex of the animals. The active compounds have proved particularly valuable in the rearing and keeping of young animals and fattening animals. The following stock animals and pets may be mentioned as examples of animals for which the active compounds can be used for promoting and accelerating growth and for improving feed utilization: warm-blooded animals, such as cattle, pigs, horses, sheep, goats, cats, dogs and rabbits; fur-bearing animals, for example mink and chinchillas; poultry, for example chicken, geese, ducks, turkeys, pigeons, parrots and canaries, and cold-blooded animals, such as fish, for example carp, and reptiles, for example snakes.

The amounts of the active compounds which are administered to the animals to achieve the desired effect can be varied substantially because of the advantageous properties of the active compounds. It is preferably about 0.01 to 50, in particular 0.1 to 10 mg/kg of body weight daily. The period of administration can be from a few hours or days up to several years. The amount of the active compound to be administered and the corresponding period of administration depend, in particular, on the species, sex, state of health and nature of housing and feeding of the animals and can easily be determined by any expert.

The active compounds are administered to the animals by the customary methods. The nature of the administration depends, in particular, on the species, behaviour and state of health of the animals. Thus, administration can be effected orally or parenterally once or several times daily at regular or irregular intervals. For reasons of expediency, oral administration, in particular in the rhythm of the food and/or drik intake of the animals, is to be preferred in most cases. Food in the context of the present invention is to be understood as both solid and liquid food and also drinks and water.

The active compounds can be administered as pure substances or in formulated form, that is to say as a mixture with non-toxic inert carriers of any desired type, for example with carriers and in formulations such as are customary in nutritive preparations.

The active compounds, optionally in formulated form, are administered in a suitable form together with pharmaceutical active compounds, mineral salts, trace elements, vitamins, proteins, fats, colourants and/or flavour substances.

Oral administration together with the feed and/or drinking water is recommended, the active compound being added to all or only portions of the feed and/or drinking water, as required.

The active compounds are formulated by customary methods by simple mixing, as a pure mixture of substances, preferably in finely divided form or in formulated form in a mixture with edible non-toxic carriers, if appropriate in the form of a premix or a feed concentrate, to which the feed and/or drinking water is added.

The feed and/or drinking water can contain, for example, the active compounds in a weight concentration of about 0.01 to 50, in particular 0.1 to 10 ppm. The optimum level of the concentration of the active compounds in the feed and/or drinking water depends, in particular, on the feed and/or drinking water intake of the animals and can easily be determined by any expert.

The nature of the feed and its composition is irrelevant here. All the customary or specific feed compositions which preferably contain the usual equilibrium of energy substances and builder substances necessary for balanced nutrition can be used. The feed can be composed, for example, of vegetable substances, for example hay, beet, cereals and cereal by-products, animal substances, for example meat, fats and bone meal, fish products, vitamins, for example vitamin A, D complex and B complex, proteins, amino acids, for example DL-methionine, and inorganic substances, for example lime and sodium chloride.

Feed concentrates contain the active compounds alongside edible substances, for example rye flour, maize flour, soya bean flour or lime, optionally with further nutrients and builder substances, as well as proteins, mineral salts and vitamins. They can be prepared by the customary methods of mixing.

In premixes and feed concentrates, preferably, the active compounds can optionally also be protected from air, light and/or moisture by suitable agents which coat their surface, for example with non-toxic waxes or gelatine.

The following is an example of the composition of a feed for rearing chicks which contains an active compound according to the invention.

200 g of wheat, 340 g of corn, 361 g of coarse soy bean meal, 60 g of beef tallow, 15 g of dicalcium phosphate, 10 g of calcium carbonate, 4 g of iodinated sodium chloride, 7.5 g of a vitamin/mineral mix and 2.5 g of an active compound premix give, after thorough mixing, 1 kg of feed.

1 kg of feed mix contains: 600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains the active compounds in the desired amount, for example 10 mg, and, in addition, 1 g of DL-methionine and soy bean flour in an amount such that 2.5 g of premix are formed.

The following is an example of the composition of a feed for rearing pigs, which contains an active compound according to the invention.

630 g of shredded cereal feed (composed of 200 g of maize, 150 g of shredded barley, 150 g of shredded oats and 130 g of shredded wheat), 80 g of fish meal, 60 g of coarse soy bean meal, 60 g of tapioca meal, 38 g of brewer's yeast, 50 g of a vitamin/mineral mix for pigs (composition, for example, as for the chick feed), 30 g of linseed cake meal, 30 g of corn gluten feed, 10 g of soy bean oil, 10 g of sugar cane molasses and 2 g of an active compound premix (composition, for example, as for the chick feed) give, after thorough mixing, 1 kg of feed.

The feed mixtures described are preferably intended for rearing and fattening chicks and pigs, but they can also be used, in the same or a similar composition, for rearing and fattening other animals.

EXAMPLE 1

Benzhydryl 3-chloromethyl-7α-phenylacetamido-3-cephem-4-carboxylate 24 ml (0.3 mole) of pyridine, 400 ul of dimethylformamide and 21.6 ml (0.3 mole) of thionyl chloride are added to a solution of 103 g (0.2 mole) of benzhydryl 3-hydroxymethyl-7β-phenylacetamido-3-cephem-4-carboxylate (prepared, for example, in accordance with Helv. Chim. Acta 57, 2044 (1974)) in 3.5 l of absolute tetrahydrofuran, while cooling with ice. After 10 minutes, the mixture is concentrated on a rotary evaporator, the residue is taken up in 2 l of ethyl acetate and the mixture is extracted by shaking twice with sodium bicarbonate solution and once with water. The organic phase is extracted by stirring with 50 g each of kieselguhr and active charcoal and the extract is filtered with suction over a frit covered with silica gel. The filtrate is then dried over magnesium sulphate and concentrated, the residue is taken up in 200 ml of methylene chloride and the product is precipitated with petroleum ether.

Yield: 76 g;

$^1$H-NMR $(DCCl_3)\delta(ppm)$=7.20–7.50 (15H, m, aromatic); 6.96 (1H, s, $CHO_2$); 6.30 (1H, d, J=9 Hz, NH); 5.86 (1H, dd, J=9 Hz, J=5 Hz, H-7); 4.95 (1H, d, J=5 Hz, H-6); 4.36 (2H, bs, $DH_2$-Cl); 3.66 (1H, d, J=15 Hz, O—$CH_2$—); 3.58 (1H, d, J=15 Hz, O—$CH_2$—); 3.56 (1H, d, J=18 Hz, H-2); and 3.40 (1H, d, J=18 Hz, H-2).

EXAMPLE 2

7-Amino-3-(1-ethyl-1-pyrrolidinium)methyl-3-cephem-4-carboxylate 10 g (18.8 mmol) of benzhydryl 3-chloromethyl-7β-phenylacetamido-3-cephem-4-carboxylate are dissolved in 112 ml of absolute methylene chloride at 0° C. After addition of 56 ml of anisole and 56 ml of trifluoroacetic acid, the mixture is stirred at 0° C. for 25 minutes. It is concentrated in vacuo, 100 ml of benzene are added and the batch is stirred under a high vacuum for 1 hour. The residue is dissolved in 100 ml of absolute tetrahydrofuran, and 18.6 g (188 mmol) of N-ethylpyrrolidine are added. The solution is stirred at room temperature for 30 minutes. 100 ml of ether are added. The precipitate formed is filtered off with suction, washed with 500 ml of ether and dissolved in 50 ml of water by adding $NaHCO_3$. 4 g of immobilized penicillin G acylase are then added and the pH value is kept constant at 7.8 by addition of 4N triethylamine in ethanol. When the enzymatic splitting has ended, the acylase is filtered off and the filtrate is brought to pH 2 with concentrated hydrochloric acid. The precipitate formed is filtered off with suction over silica gel and the filtrate is added dropwise to 2 l of acetone. The desired product crystallises out as the hydrochloride and is filtered off with suction and dried.

Yield: 1.76 g ($\times$HCl$\times$$H_2O$, 25.6%).

NMR ($D_2O$): $\delta$(ppm)=5.31 (1H, d, J=5 Hz, H-7-lactam); 5.12 (1H, d, J=5 Hz, H-6-lactam); 4.62 (1H, d, J=14 Hz, $CH_2$-pyrrolidine); 3.88 (1H, d, J=14 Hz, $CH_2$-pyrrolidine); 3.86 (1H, d, J=18 Hz, S-$CH_2$); 3.58 (1H, d, J=18 Hz, S—$CH_2$); 3.42 (4H, m, pyrrolidine); 3.24 (2H, q, J=7 Hz, —$CH_2$—N$^+$—); 2.06 (4H, m, pyrrolidine); and 1.24 (3H, t, J=7 Hz, $CH_3$).

EXAMPLE 3

7β-[(Z)-2-(2-Aminothiazol-4-yl)-2-methoxyiminoacetamido]-3-(1-ethyl-1-pyrrolidinium)methyl-3-cephem-4-carboxylate 353 mg (1.76 mmol) of (Z)-2-(2-aminothiazol-4-yl)-2-methoxyiminoacetic acid are dissolved in 2.7 ml of absolute dimethylformamide under nitrogen at room temperature. After addition of 113 μl of N-ethyldiisopropylamine, 123 μl of tripropylamine and 152 μl of tributylamine, the mixture is cooled to −50° C. 145 μl of methanesulphonyl chloride are added and the solution is stirred at −50° C. for 30 minutes. This solution is then added rapidly to a solution, cooled to 0° C., of 470 mg (1.35 mmol) of 7-amino-3-(1-ethyl-1-pyrrolidinium)-methyl-3-cephem-4-carboxylate ($\times$HCl) in 0.85 ml of water and 0.7 ml of triethylamine. After 5 minutes, the reaction solution is added to 150 ml of acetone. The precipitate formed is filtered off with suction, dried and chromatographed over adsorber resin HP 20 (eluting agent: acetonitrile/water 5/95).

Yield: 400 mg (59%)

¹H-NMR (D₆-DMSO): δ(ppm)=9.63 (1H, d, J=9 Hz, NH); 7.28 (2H, bs, NH₂); 6.78 (1H, s, thiazole); 5.69 (1H, dd, J=9 Hz, J=5 Hz, H-7-lactam); 5.15 (1H, d, J=5 Hz, H-6-lactam); 5.08 (1H, d, J=14 Hz, CH₂-pyrrolidine); 3.88 (1H, s, OCH₃); 3.85 (1H, d, J=14 Hz, CH₂-pyrrolidine); 3.81 (1H, d, J=18 Hz, S—CH₂); 3.20-3.50 (7H, m, S—CH₂, —CH₂—N—, pyrrolidine); 2.04 (4H, m, pyrrolidine); and 1.28 (3H, t, J=7 Hz, CH₃).

EXAMPLE 4

7-Amino-3-(1-ethyl-1-piperidinium)methyl-3-cephem-4-carboxylate

This compound is prepared analogously to Example 2 from benzhydryl 3-chloromethyl-7β-phenylacetamido-3-cephem-4-carboxylate and N-ethylpiperidine.

¹H-NMR (D₂O): δ(ppm)=5.31 (1H, d, J=5 Hz, H-7-lactam); 5.10 (1H, d, J=5 Hz, H-6-lactam); 4.59 (1H, d, J=15 Hz, CH₂-piperidine); 3.89 (1H, d, J=18 Hz, S—CH₂); 3.87 (1H, d, J=15 Hz, CH₂-piperidine); 3.45 (1H, d, J=18 Hz, S—CH₂); 3.34 (2H, q, J=7 Hz, —CH₂+N—); 3.00-3.20 (4H, m, piperidine); 1.40-1.70 (6H, m, piperidine); and 1.19 (3H, t, J=7 Hz, CH₃).

EXAMPLE 5

7β-[(Z)-2-(2-Aminothiazol-4-yl)-2-methoxyiminoacetamido]-3-(1-ethyl-1-piperidinium)methyl-3-cephem-4-carboxylate This compound is prepared analogously to Example 3 from (Z)-2-(2-aminothiazol-4-yl)-2-methoxyiminoacetic acid and 7-amino-3-(1-ethyl-1-piperidinium)methyl-3-cephem-4-carboxylate.

¹H-NMR (D₆-DMSO): δ(ppm)=9.65 (1H, d, J=9 Hz, NH); 7.26 (2H, bs, NH₂); 6.77 (1H, s, thiazole); 5.70 (1H, dd, J=9 Hz, J=5 Hz, H-7-lactam); 5.13 (1H, d, J=5 Hz, H-6-lactam); 5.10 (1H, d, J=14 Hz, CH₂-piperidine); 3.80-3.90 (5H, m, OCH₃, CH₂-piperidine, S—CH₂); 3.30-3.50 (7H, m, S—CH₂—N—, piperidine); 1.40-1.80 (6H, m, piperidine); and 1.19 (3H, t, J=7 Hz, CH₃).

EXAMPLE 6

3-[(1-2-Hydroxyethyl)-1-pyrrolidinium]methyl-7β-phenylacetamido-3-cephem-4-carboxylate 4.68 g (12 mmol) of 3-acetoxymethyl-7β-phenylacetamido-3-cephem-4-carboxylic acid are suspended in 48 ml of absolute methylene chloride under nitrogen at room temperature and are dissolved by addition of 7.6 ml (36 mmol) N-methyl-N-trimethyl-silyltrifluoroacetamide (MSTFA). After cooling to 0° C., 7 ml (48 mmol) of trimethylsilyl iodide are added and the reaction solution is stirred at 0° C. for 1 hour. After addition of 7.6 ml of absolute tetrahydrofuran, the mixture is stirred at 0° C. for a further 15 minutes. 14.4 ml (120 mmol) of N-(2-hydroxyethyl)pyrrolidine are then added and the solution is subsequently stirred for 30 minutes. 2.4 ml of water are then added and, after a further 5 minutes, the mixture is poured onto 200 ml of ether. The ether is decanted off from the oily residue, the residue is stirred again with ether and, after decanting again, is taken up in water, and the mixture is chromatographed over adsorber resin HP 20 (eluting agent: acetonitrile/water 5/95).

Yield: 3.6 g (68%).

¹H-NMR (D₆-DMSO): δ(ppm)=9.13 (1H, d, J=9 Hz, NH); 7.28 (5H, m, aromatic); 5.55 (1H, dd, J=9 Hz, J=5 Hz, H-7-lactam); 5.06 (1H, d, j=5 Hz, H-6-lactam); 5.04 (1H, d, J=14 Hz, CH₂-pyrrolidine); 3.95 (1H, d, J=14 Hz, CH₂-pyrrolidine); 3.33-3.85 (12H, m); and 2.04 (4H, m, pyrrolidine).

EXAMPLE 7

7-Amino-3-[1-(2-hydroxyethyl)-1-pyrrolidinium]methyl-3-cephem-4-carboxylate 4 g of immobilized penicillin G acylase are added to a solution of 3.5 g (7.8 mmol) of 3-[1-(2-hydroxyethyl-1-pyrrolidinium]methyl-7β-phenylacetamido-3-cephem-4-carboxylate in 100 ml of water and the pH value is kept constant at 7.8 by adding 4N triethylamine in ethanol. When the enzymatic splitting has ended, the acylase is filtered off and the filtrate is brought to pH 2 with concentrated hydrochloric acid. The precipitate formed is filtered off with suction over silica gel and the filtrate is added dropwise to 2 l of acetone. the desired product crystallizes out as the hydrochloride and is filtered off with suction and dried.

Yield: 1.9 g (×HCl×H₂O, 64%).

¹H-NMR (D₆-DMSO): δ(ppm)=5.33 (1H, d, J=5 Hz, H-7-lactam); 5.13 (1H, d, J=5 Hz, H-6-lactam); 4.70 (1H, d, J=14 Hz, CH₂-pyrrolidine); 3.93 (2H, m, CH₂—OH); 3.87 (1H, d, J=18 Hz, S—CH₂); 3.30-3.70 (7H, m); and 2.11 (4H, m, pyrrolidine).

EXAMPLE 8

7β-[(Z)-2-(2-Aminothiazol-4-yl)-2-methoxyiminoacetamido]-3-[1-(2-hydroxyethyl)-1-pyrrolidinium]methyl-3-cephem-4-carboxylate This compound is prepared analogously to Example 3 from (Z)-2-(2-aminothiazol-4-yl)-2-methoxyiminoacetic acid and 7-amino-3-[1-(2-hydroxyethyl)-1-pyrrolidinium]methyl-3-cephem-4-carboxylate.

¹H-NMR (D₆-DMSO): δ(ppm)=9.58 (1H, d, J=) Hz, NH); 9.24 (2H, bs, NH₂); 6.71 (1H, s, thiazole); 5.64 (1H, dd, J=9 Hz, J=5 Hz, H-7-lactam); 5.11 (1H, d, J=5 Hz, H-6-lactam); 5.03 (1H, d, J=13 Hz, CH₂-pyrrolidine); 3.93 (1H, d, J=13 Hz, CH₂-pyrrolidine); 3.81 (3H, s, OCH₃); 3.80 (2H, m, CH₂—OH); 3.77 (1H, d, J=18 Hz, S—CH₂); 3.30-3.60 (7H, m); and 2.01 (4H, m, pyrrolidine).

EXAMPLE 9

3-[1-(2-Hydroxyethyl)-1-piperidinium]methyl-7β-phenylacetamido-3-cephem-4-carboxylate This compound is prepared analogously to Example 6 from 3-acetoxymethyl-7β-phenylacetamido-3-cephem-4-carboxylic acid and N-(2-hydroxyethyl)-piperidine.

¹H-NMR (D₆-DMSO): δ(ppm)=9.17 (1H, d, J=9 Hz, NH); 7.30 (5H, m, aromatic); 5.56 (1H, dd, J=9 Hz, J=5 Hz, H-7-lactam); 5.09 (1H, d, J=5 Hz, H-6-lactam); 5.08 (1H, d, J=13 Hz, CH₂-piperidine); 3.10-3.90 (12H, m); and 1.40-1.90 (6H, m).

EXAMPLE 10

7-Amino-3-[1-(2-hydroxyethyl)-1-piperidinium]methyl-3-cephem-4-carboxylate

This compound is prepared analogously to Example 7 from 3-[1-(2-hydroxyethyl)-1-piperidinium]methyl-7β-phenylacetamido-3-cephem-4-carboxylate.

¹H-NMR (D₂O): δ(ppm)=5.34 (1H, d, J=5 Hz, H-7-lactam); 5.14 (1H, d, J=5 Hz, H-6-lactam); 4.75 (1H, d, J=14 Hz, CH₂-piperidine); 3.96 (2H, m, CH₂-OH); 3.91 (1H, d, J=18 Hz, S-CH₂); 3.10-3.60 (7H, m); and 1.40-1.90 (6H, m, piperidine).

EXAMPLE 11

7β-[(Z)-2-(2-Aminothiazol-4-yl)-2-methoxyiminoactamido]-3-[1-(2-hydroxyethyl)-1-piperidinium]methyl-3-cephem-4-carboxylate This compound is prepared analogously to Example 3 from (Z)-2-(2-aminothiazol-4-yl)-2-methoxyiminoacetic acid and 7-amino-3-[1-(2-hydroxyethyl)-1-piperidinium]methyl-3-cephem-4-carboxylate.

$^1$H-NMR (D$_6$-DMSO): δ(ppm)=9.61 (1H, d, J=9 Hz, NH); 7.26 (2H, bs, NH$_2$); 6.74 (1H, s, thiazole); 5.67 (1H, dd, J=9 Hz, J=5 Hz, H-7-lactam); 5.15 (1H, d, J=5 Hz, H-6-lactam); 5.09 (1H, d, J=14 Hz, CH$_2$-piperidine); 4.01 (1H, d, J=14 Hz, CH$_2$piperidine); 3.84 (3H, s, OCH$_3$); 3.80 (3H, m); 3.10–3.50 (7H, m); and 1.40–1.90 (6H, m, piperidine).

EXAMPLE 12

3-[4-(2-Hydroxyethyl)-4-morpholinium]methyl-7β-phenylacetamido-3-cephem-4-carboxylate This compound is prepared analogously to Example 6 from 3-acetoxymethyl-7β-phenylacetamido-3-cephem-4-carboxylic acid and N-(2-hydroxyethyl)morpholine.

$^1$H-NMR (DMSO-D$_6$): δ(ppm)=9.19 (1H, d, J=9 Hz, NH); 7.34 (5H, m, aromatic); 5.62 (1H, dd, J=9 Hz, J=5 Hz, H-7-lactam); 5.20 (1H, d, J=14 Hz, CH$_2$-morpholine); 5.13 (1H, d, J=5 Hz, H-6-lactam); 4.16 (1H, d, J=14 Hz, CH$_2$-morpholine); and 3.30–4.10 (16H, m).

EXAMPLE 13

7-Amino-3-[4-(2-hydroxyethyl)-4-morpholinium]methyl-3-cephem-4-carboxylate

This compound is prepared analogously to Example 7 from 3-[4-(2-hydroxyethyl)-4-morpholinium]methyl-7β-phenylacetamido-3-cephem-4-carboxylate.

$^1$H-NMR (D$_2$O): δ(ppm)=5.36 (1H, d, J=5 Hz, H-7-lactam); 5.15 (1H, d, J=5 Hz, H-6-lactam); 4.88 (1H, d, J=14 Hz, CH$_2$-morpholine); 4.21 (1H, d, J=14 Hz, CH$_2$-morpholine); and 3.30–4.10 (14H, m).

EXAMPLE 14

7β-[(Z)-2-(2-Aminothiazol-4-yl)-2-methoxyiminoacetamido]-3-[4-(2-hydroxyethyl)-4-morpholinium]methyl-3-cephem-4-carboxylate This compound is prepared analogously to Example 3 from (Z)-2-(2-aminothiazol-4-yl)-2-methoxyiminoacetic acid and 7-amino-3-[4-(2-hydroxyethyl)-4-morpholinium]methyl-3-cephem-carboxylate.

$^1$NMR (DMSO-D$_6$): δ(ppm)=9.63 (1H, d, J=9 Hz, NH); 7.28 (2H, bs, NH$_2$); 6.77 (1H, s, thiazole); 5.71 (1H, dd, J=9 Hz, J=5 Hz, H-7-lactam); 5.21 (1H, d, J=14 Hz, CH$_2$-morpholine); 5.11 (1H, d, J=5 Hz, H-6-lactam); 4.13 (1H, d, J=14 Hz, CH$_2$-morpholine); 3.87 (3H, s, OCH$_3$); and 3.30–4.00 (14H, m).

EXAMPLE 15

7-Amino-3-(4-ethyl-4-morpholinium)methyl-3-cephem-4-carboxylate

This compound is prepared analogously to Example 17 from benzhydryl 3-chloromethyl-7β-phenylacetamdio-3-cephem-4-carboxylate.

$^1$H-NMR (DMSO-d$_6$): δ(ppm)=5.35 (1H, d, J=5 Hz, H-7-lactam); 5.16 (1H, d, J=5 Hz, H-6-lactam); 4.58 (1H, d, J=14 Hz, CH$_2$-morpholine); 4.02 (1H, d, J=14 Hz, CH$_2$ morpholine); 3.96 (4H, m, morpholine); 3.90 (1H, d, J=18 Hz, S-CH$_2$); 3.30–3.60 (7H, m, S-CH$_2$, morpholine,

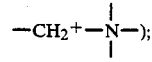

and 1.24 (3H, t, J=7 Hz, CH$_3$).

EXAMPLE 16

7β[(Z)-2-(2-Aminothiazol-4-yl)-2-methoxyiminoacetamido]-3-(4-ethyl-4-morpholinium)methyl-3-cephem-4-carboxylate This compound is prepared analogously to Example 3 from (Z)-2-(2-aminothiazol-4-yl)-2-methoxyiminoacetic acid and 7-amino-3-(4-ethyl-4-morpholinium)methyl-3-cephem-4-carboxylate $^1$H-NMR (DMSO-d$_6$): δ(ppm)=9.59 (1H, d, J=9 Hz, NH); 7.25 (2H, bs, NH$_2$); 6.76 (1H, s, thiazole); 5.69 (1H, dd, J=9Hz, J=5 Hz, H-7-lactam); 5.23 (1H, d, J=13 Hz, CH$_2$-morpholine); 5.16 (1H, d, J=5 Hz, H-6-lactam), 3.80–4.00 (6H, m, CH$_2$-morpholine, morpholine, S-CH$_2$); 3.86 (3H, s, OCH$_3$); 3.30–3.60 (7H, m, S-CH$_2$, morpholine, —CH$_2$—N—); and 1.25 (3H, t, J=7 Hz, CH$_3$).

EXAMPLE 17

7-Amino-3-(1-propyl-1-pyrrolidinium)methyl-3-cephem-4-carboxylate

This compound is prepared analogously to Example 17 from benzhydryl 3-chloromethyl-7β-phenylacetamido-3-cephem-4-carboxylate and N-propylpyrrolidine.

$^1$H-NMR (D$_2$O): δ(ppm)=5.33 (1H, d, J=5 Hz, H-7-lactam); 5.15 (1h, d, J=5 Hz, H-6-lactam); 4.63 (1H, d, J=13 Hz, CH$_2$-pyrrolidine); 3.96 (1H, d, J=13 Hz, CH$_2$-pyrrolidine); 3.88 (1H, d, J=18 Hz, S-CH$_2$); 3.55 (1H, d, J=18 Hz, S-CH$_2$); 3.45 (4H, m, pyrrolidine); 3.12 (2H, m,

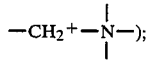

2.10 (4H, m, pyrrolidine; 1.66 (2H, m, —CH$_2$); and 0.85 (3H, m, CH$_3$).

EXAMPLE 18

7β-[(Z)-2-(2-Aminothiazol-4-yl)-2-methoxyiminoacetamido]-3-(1-propyl-1-pyrrolidinium)methyl)-3-cephem-4-carboxylate This compound is prepared analogously to Example 3 from (Z)-2-(2-aminothiazol-4-yl)-2-methoxyiminoacetic acid and 7-amino-3-(1-propyl-1-pyrrolidinium)methyl-3-cephem-4-carboxylate.

$^1$H-NMR (DMSO-d$_6$): δ(ppm)=9.58 (1H, d, J=9 Hz, NH); 7.24 (2H, bs, NH$_2$); 6.75 (1H, s, thiazole); 5.67 (1H, dd, J=9 Hz, J=5 Hz, H-7-lactam); 5.13 (1H, d, J=5 Hz, H-6-lactam); 5.08 (1H, d, J=13 Hz, CH$_2$-pyrrolidine); 3.86 (3H, s, OCH$_3$); 3.80 (2H, m, CH$_2$-pyrrolidine, S—CH$_2$); 3.45 (5H, m, pyrrolidine, S—CH$_2$); 3.13 (2H, m,

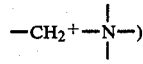

2.03 (4H, m, pyrrolidine); 1.74 (2H, m, —CH₂—); and 0.90 (3H, t, J=7 Hz, CH₃).

EXAMPLE 19

7-Amino-3-(1-isopropyl-1-pyrrolidinium)methyl-3-cephem-4-carboxylate

This compound is prepared analogously to Example 2 from benzhydryl 3-chloromethyl-7β-phenylacetamido-3-cephem-4-carboxylate and N-isopropylpyrrolidine.

¹H-NMR (D₂O): δ (ppm)=5.35 (1H, d, J=5 Hz, H-7-lactam); 5.13 (1H, d, J=5 Hz, H-6-lactam); 4.02 (1H, d, J=13 Hz, CH₂-pyrrolidine); 3.93 (1H, d, J=18 Hz, S—CH₂); 3.40-3.80 (6H, m, S—CH₂, pyrrolidine,

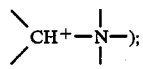

2.10 (4H, m, pyrrolidine); and 1.43 (6H, m, isopropyl).

EXAMPLE 20

7β-[(Z)-2-(2-Aminothiazol-4-yl)-2-methoxyiminoacetamido]-3-(1-isopropyl-1-pyrrolidinium)-methyl-3-cephem-4-carboxylate This compound is prepared analogously to Example 3 from (Z)-2-(2-aminothiazol-4-yl)-2-methoxyiminoacetic acid and 7-amino-3-(1-isopropyl-1-pyrrolidinium)methyl-3-cephem-4-carboxylate.

¹H-NMR (DMSO-d₆): δ (ppm)=9.61 (1H, d, J=9 Hz, NH); 7.28 (2H, s, NH₂); 6.77 (1H, s, thiazole); 5.67 (1H, dd, J=9 Hz, J=5 Hz, H-7-lactam); 5.17 (1H, d, J=5 Hz, H-6-lactam); 4.96 (1H, d, J=13 Hz, CH₂-pyrrolidine); 3.92 (1H, d, J=13 Hz, CH₂-pyrrolidine); 3.87 (3H, s, OCH₃); 3.83 (1H, d, J=18 Hz, S—CH₂); 3.40-3.70 (6H, m,

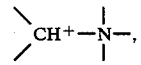

pyrrolidine, S—CH₂); 1.98 (4H, m, pyrrolidine); and 1.35 (6H, m, isopropyl).

EXAMPLE 21

7-Amino-3-(1-butyl-1-pyrrolidinium)methyl-3-cephem-4-carboxylate

This compound is prepared analogously to Example 2 from benzhydryl 3-chloromethyl-7β-phenylacetamido-3-cephem-4-carboxylate and N-butyl-pyrrolidine.

¹H-NMR(D₂O): δ (ppm)=5.24 (1H, d, J=5 Hz, H-7-lactam); 5.04 (1H, d, J=5 Hz, H-6-lactam); 4.58 (1H, d, J=13 Hz, CH₂-pyrrolidine); 3.85 (1H, d, J=13 Hz, CH₂-pyrrolidine); 3.82 (1H, d, J=18 Hz, S—CH₂); 3.43 (1H, d, J=18 Hz, S—CH₂); 3.28 (4H, m, pyrrolidine); 3.07 (2H, m,

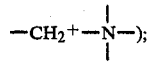

2.04 (4H, m, pyrrolidine); 1.58 (2H, m, —CH₂—); 1.18 (2H, m, —CH₂—); and 0.80 (3H, t, J=7 Hz, CH₃).

EXAMPLE 22

7β-[(Z)-2-(2-Aminothiazol-4-yl)-2-methoxyiminoacetamido]-3-(1-butyl-1-pyrrolidinium)methyl-3-cephem-4-carboxylate This compound is prepared analogously to Example 3 from (Z)-2-(2-aminothiazol-4-yl)-2-methoxyiminoacetic acid and 7-amino-3-(1-butyl-1-pyrrolidinium)methyl-3-cephem-4-carboxylate.

¹H-NMR (DMSO-d₆): δ (ppm)=9.58 (1H, d, J=9 Hz, NH); 7.21 (1H, bs, NH₂); 6.71 (1H, s, thiazole); 5.62 (1H, dd, J=9 Hz, J=5 Hz, H-7-lactam); 5.10 (1H, d, J=5 Hz, H-6-lactam); 5.05 1H, d, J=13 Hz, CH₂-pyrrolidine); 3.86 (3H, s, OCH₃); 3.82 (2H, m, CH₂-pyrrolidine, S—CH₂); 3.30 (5H, m, S—CH₂, pyrrolidine); 3.13 (2H, m,

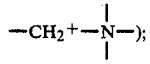

2.01 (4H, m, pyrrolidine); 1.70 (2H, m, —CH₂—); 1.27 (2H, m, —CH₂); and 0.90 (3H, t, J=7 Hz, CH₃).

EXAMPLE 23

3-[1-(3-Hydroxypropyl)-1-pyrrolidinium]methyl-7β-phenylacetamido-3-cephem-4-carboxylate This compound is prepared analogously to Example 6 from 3-acetoxymethyl-7β-phenylacetamido-3-cephem-4-carboxylic acid and N-(3-hydroxypropyl)-pyrrolidine.

¹H-NMR (D₆-DMSO): δ (ppm)=9.16 (1H, d, J=9 Hz, NH); 7.30 (5H, aromatic); 5.58 (1H, dd, J=9 Hz, J=5 Hz, H-7-lactam); 5.08 (1H, d, J=5 Hz, H-6-lactam); 5.03 (1H, d, J=13 Hz, CH₂-pyrrolidine); 3.88 (1H, d, J=13 Hz, CH₂-pyrrolidine); 3.84 (1H, d, J=18 Hz, S—CH₂); 2.90-3.60 (11H, m); and 1.80-2.10 (6H, m).

EXAMPLE 24

7-Amino-3-[1-(3-hydroxypropyl)-1-pyrrolidinium]-methyl-3-cephem-4-carboxylate

This compound is prepared analogously to Example 7 from 3-[1-(3-hydroxypropyl)-1-pyrrolidinium]methyl-3-cephem-4-carboxylate.

¹H-NMR(D₂O): δ (ppm)=5.31 (1H, d, J=5 Hz, H-7-lactam); 5.11 (1H, d, J=5 Hz, H-6-lactam); 4.63 (1H, d, J=13 Hz, CH₂-pyrrolidine); 3.96 (1H, d, J=13 Hz, CH₂-pyrrolidine); 3.88 (1H, d, J=18 Hz, S—CH₂); 3.40-3.60 (9H, m); 2.08 (4H, m, pyrrolidine); and 1.92 (2H, m, —CH₂—).

EXAMPLE 25

7β-[(Z)-2-(2-Aminothiazol-4-yl)-2-methoxyiminoacetamido]-3-[1-(3-hydroxypropyl)-1-pyrrolidinium]methyl-3-cephem-4-carboxylate This compound is prepared analogously to Example 3 from (Z)-2-(2-aminothiazol-4-yl)-2-methoxyiminoacetic acid and 7-amino-3-[1-(3-hydroxypropyl)1-pyrrolidinium]methyl-3-cephem-4-carboxylate.

$^1$H-NMR (DMSO-d$_6$): (ppm)=9.59 (1H, d, J=9 Hz, NH); 7.26 (2H, bs, NH$_2$); 6.75 (1H, s, thiazole); 5.68 (1H, dd, J=9 Hz, J=5 Hz, H-7-lactam); 5.13 (1H, d, J=5 Hz, H-6-lactam); 5.05 (1H, d, J=13 Hz, CH$_2$-pyrrolidine); 3.86 (3H, s, OCH$_3$); 3.84 (2H, m, CH$_2$-pyrrolidine, S—CH$_2$); 3.20–3.60 (9H, m, S—CH$_2$, —CH$_2$—N—, —CH$_2$OH' pyrrolidine); and 1.88 (2H, m, —CH$_2$—).

EXAMPLE 26

3-{1-[2-(2-Hydroxyethoxy)ethyl]-1-pyrrolidinium} methyl-7β-phenylacetamido-3-cephem-4-carboxylate This compound is prepared analogously to Example 6 from 3-acetoxymethyl-7β-phenylacetamido-3-cephem-4-carboxylic acid and N-[2-(2-hydroxyethoxy)ethyl]-pyrrolidine.

$^1$H-NMR (D$_6$-DMSO): δ (ppm)=9.15 (1H, d, J=9 Hz, NH); 7.31 (5H, m, aromatic); 5.57 (1H, dd, J=9 Hz, J=5 Hz, H-7-lactam); 5.15 (1H, d, J=13 Hz, CH$_2$-pyrrolidine); 5.08 (1H, d, J=5 Hz, H-6-lactam); 3.99 (1H, d, J=13 Hz, CH$_2$-pyrrolidine); 2.90–3.90 (14H, m); and 2.08 (4H, m, pyrrolidine).

EXAMPLE 27

7-Amino-3-{1-[2-(2-hydroxyethoxy)ethyl]-1-pyrrolidinium}methyl-3-cephem-4-carboxylate This compund is prepared analogously to Example 7 from 3-{1-[2-(2-hydroxyethoxy)ethyl]-1-pyrrolidinium} methyl-7β-phenylacetamido-3-cephem-4-carboxylate.

$^1$H-NMR (D$_2$O): δ (ppm)=5.25 (1H, d, J=5 Hz, H-7-lactam); 5.07 (1H, d, J=5 Hz, H-6-lactam); 4.65 (1H, d, J=13 Hz, CH$_2$-pyrrolidine); 4.04 (1H, d, J=13 Hz, CH$_2$-pyrrolidine); 3.82 (1H, d, J=18 Hz, S—CH$_2$); 3.30–380 (9H, m); and 2.05 (4H, m, pyrrolidine).

EXAMPLE 28

7β-[(Z)-2-(2-Aminothiazol-4-yl)-2-methoxyiminoacetamido]-3-{1-[2-(2-hydroxyethoxy)ethyl]1-pyrrolidInium}methyl-3-cephem-4-carboxylate This compound is prepared analogously to Example 3 from (Z)-2-(2-aminothiazol-4-yl)-2-methoxyiminoacetic acid and 7-amino-3-{1-[2-(2-hydroxyethoxy)ethyl]-1-pyrrolidinium}methyl-3-cephem-4-carboxylate.

$^1$H-NMR (DMSO-d$_6$): δ (ppm)=9.60 (1H, d, J=9 Hz, NH); 7.27 (2H, bs, NH$_2$); 6.74 (1H, s, thiazole); 5.67 (1H, dd, J=9 Hz, J=5 Hz, H-7-lactam); 5.16 (1H, d, J=13 Hz, CH$_2$-pyrrolidine); 5.14 (1H, d, J=5 Hz, H-6-lactam); 3.98 (1H, d, J=13 Hz, CH$_2$-pyrrolidine); 3.84 (3H, s, OCH$_3$); 3.80 (3H, m); 3.30–3.60 (11H, m); and 2.05 (4H, m, pyrrolidine).

EXAMPLE 29

3-[1-(2-Hydroxy-2-phenylethyl)1-pyrrolidinium]methyl-7β-phenylacetamido-3-cephem-4-carboxylate This compound is prepared analogously to Example 6 from 3-acetoxymethyl-7β-phenylacetamido-3-cephem-4-carboxylic acid and DL-N-(2-hydroxy-2-phenylethyl)pyrrolidine. A mixture of two diastereoisomers is obtained.

$^1$H-NMR (D$_6$-DMSO): δ (ppm)=9.14 (1H, d, J=9 Hz, NH); 7.20–7.60 (10H, m, aromatic); 5.58 (1H, m H-7-lactam); 5.33 (1H, m, CH—OH); 5.19 (1H, m, CH$_2$-pyrrolidine); 5.07 (1H, d, J=5 Hz, H-6-lactam); 4.36 and 4.21 (1H, d, J=13 Hz, CH$_2$-pyrrolidine); 3.10–390 (10H, m); and 2.10 (4H, m, pyrrolidine).

EXAMPLE 30

7-Amino-3-[1-(2-hydroxy-2-phenylethyl)-1-pyrrolidinium]methyl-3-cephem-4-carboxylate This compound is prepared analogously to Example 7 from 3-[1-(2-hydroxy-2-phenylethyl)-1-pyrrolidinium]-methyl-3-cephem-4-carboxylate (mixture of two diastereoisomers).

$^1$H-NMR (D$_2$O): δ (ppm)=7.40 (5H, bs, aromatic); 5.30 (2H, m, H-7-lactam, CH—OH); 5.14 (1H, m H-6-lactam); 4.82 (1H, m, CH$_2$-pyrrolidine); 4.55 and 4.37 (1H, d, J=13 Hz, CH$_2$-pyrrolidine); 3.30–4.00 (8H, m); and 2.16 (4H, bs, pyrrolidine).

EXAMPLE 31

7β-[(Z)-2-(2-Aminothiazol-4-yl)-2-methoxyiminoacetamido]-3-[1-(2-hydroxy-2-phenylethyl)-1-pyrrolidinium]methyl-3-cephem-4-carboxylate This compound is prepared analogously to Example 3 from (Z)-2-(2-aminothiazol-4-yl)-2-methoxyiminoacetic acid and 7-amino-3-[1-(2-hydroxy-2-phenylethyl)-1-pyrrolidinium]methyl-3-cephem-4-carboxylate (mixture of two diastereoisomers).

$^1$H-NMR (DMSO-d$_6$): δ (ppm)=9.58 (1H, d, J=9 Hz, NH); 7.30–7.50 5H, m, aromatic); 7.22 (2H, bs, NH$_2$); 6.72 and 6.73 (1H, s, thiazole); 5.63 (1H, m, H-7-lactam); 5.08–5.30 (3H, CH—OH, CH$_2$-pyrrolidine, H-6-lactam); 4.29 and 4.13 (1H, d, J=13 Hz, CH$_2$-pyrrolidine); 3.82 (3H, s, OCH$_3$); 3.20–3.80 (8H, m; and 2.05 (4H, m, pyrrolidine).

It will be understood that the specification and examples are illustrative but not limitative of the present invention and that other embodiments within the spirit and scope of the invention will suggest themselves to those skilled in the art.

We claim:

1. A cephalosporin which is selected from the group consisting of

7β-[(Z)-2-(2-Aminothiazol-4-yl)-2-methoxyiminoacetamido]-3-(1-ethyl-1-piperidinium)methyl-3-cephem-4-carboxylate and 7β[(Z)-2-(2-Aminothiazol-4-yl)-2-methoxyiminoacetamido]-3-(4-ethyl-4-morpholinium)methyl-3-cephem-4-carboxylate or a pharmaceutically acceptable salt thereof.

2. An antibacterial composition comprising an antibacterially effective amount of a compound or salt according to claim 1 and a diluent.

3. A unit dose of a composition according to claim 1, in the form of a tablet, capsule or ampule.

4. A method of combatting bacteria which comprises applying to such bacteria or to a bacteria habitat an antibacterially effective amount of a cephalosporin or salt according to claim 1.

5. An animal growth promoting composition comprising an animal growth promoting-effective amount of a compound or salt according to claim 1 and an animal foodstuff as a diluent.

* * * * *